United States Patent [19]

Hobbs

[11] Patent Number: 4,813,932
[45] Date of Patent: Mar. 21, 1989

[54] SINGLE-HANDED BREAST PUMP

[76] Inventor: Michael A. Hobbs, 79 Monkhams Dr., Woodford Green, Essex, England

[21] Appl. No.: 97,362

[22] Filed: Sep. 11, 1987

Related U.S. Application Data

[63] Continuation of Ser. No. 772,923, Sep. 5, 1985, abandoned.

[30] Foreign Application Priority Data

Sep. 11, 1984 [GB] United Kingdom ............... 8422861

[51] Int. Cl.⁴ ............................................. A61M 1/06
[52] U.S. Cl. ..................................... 604/74; 604/346; 222/383
[58] Field of Search .......................... 604/73, 74, 346; 222/383, 385; 92/129

[56] References Cited

U.S. PATENT DOCUMENTS

| | | | |
|---|---|---|---|
| 897,289 | 9/1908 | Howell | 604/74 |
| 1,484,874 | 2/1924 | Castillo | 604/74 |
| 1,509,226 | 9/1924 | Brown | 604/74 |
| 2,419,795 | 4/1947 | Saunders | 604/74 |
| 3,782,385 | 1/1974 | Loyd | 604/74 |
| 4,311,141 | 1/1982 | Diamond | 604/74 |
| 4,312,351 | 1/1982 | Kurtz | 604/321 |
| 4,583,970 | 4/1986 | Kirchner | 604/74 |

FOREIGN PATENT DOCUMENTS

| | | | |
|---|---|---|---|
| 762701 | 12/1956 | United Kingdom | 604/74 |
| 2127293 | 4/1984 | United Kingdom | 604/74 |

Primary Examiner—C. Fred Rosenbaum
Assistant Examiner—J. L. Kruter
Attorney, Agent, or Firm—Wolf, Greenfield & Sacks

[57] ABSTRACT

A single handed breast pump comprises a pump body (1) housing a piston (7) releasably connected to a hand lever (9) itself releasably pivoted to the pump body, the latter including a funnel (2) to be laid against the nipple and an outlet (4) at which a container may be connected. The funnel connects with a variable volume chamber in the pump body, said chamber having valves (11, 24) respectively for venting and for opening communication with the container outlet, whereby on operation of the hand lever an alternating pressure can be built up and relieved at the funnel.

16 Claims, 5 Drawing Sheets

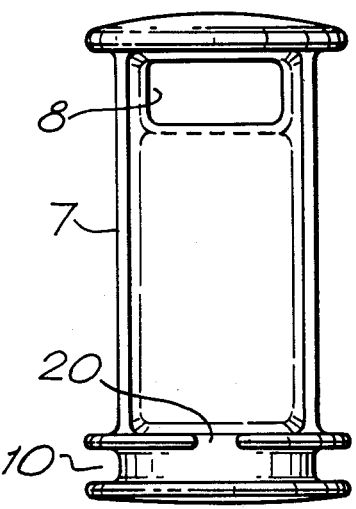
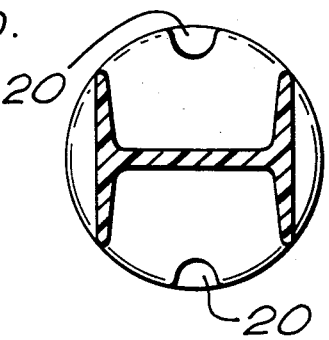
FIG.5.
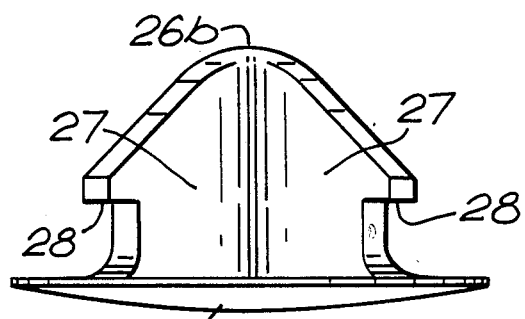
FIG.6.
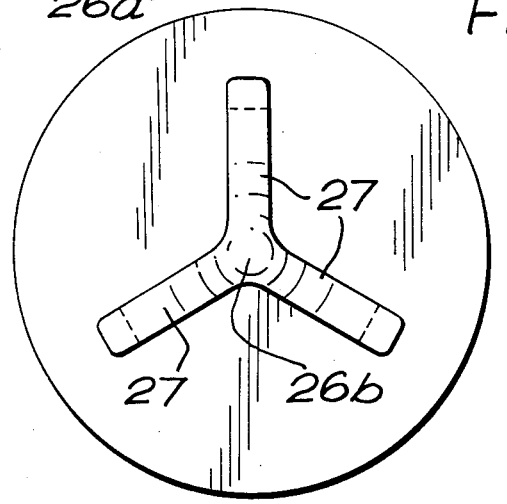

SINGLE-HANDED BREAST PUMP

BACKGROUND OF THE INVENTION

This application is a continuation of application Ser. No. 772,923, filed Sept. 5, 1985, now abandoned.

This invention relates to a breast pump and more particularly to a pump which can be operated by the user with one hand only so that the hand holding the pump against the breast is also used to actuate negative pressure generating means to cause milk to be expressed from the nipple.

Numerous breast pumps are known but they are complicated in construction and not readily adapted to be dismantled for sterilisation purposes. They also normally require the user to hold the pump against the breast with one hand and operate the negative pressure generating means with the other. As it is desirable to stimulate the breast in some way to encourage lactation, the users other hand is often needed for this purpose so it is not free for use to activate the negative pressure generating means. To overcome this problem, motor driven pumps have been used but they are expensive to manufacture and cannot readily be dismantled for sterilisation purposes.

It is an object of the invention therefore to provide a breast pump capable of operation using only one hand, which is simple in construction and readily dismantable so that the various parts thereof may be cleaned and/or sterilised.

SUMMARY OF THE INVENTION

According to the invention there is provided a single handed breast pump comprising a body provided with a first part shaped to receive the nipple portion of a breast therein and a second part for the connection of a container to collect expressed milk, the body housing manually operable means to create an alternating pressure at the nipple sufficient to express milk therefrom, said means including a valve system operable so that only the volume in the region of the nipple is subjected to said alternating pressure, the pump being constructed and arranged so that it may be held against the nipple by the user with one hand only, said same hand being used to manually operate the means to create the alternating pressure.

Preferably, the manually operable alternating pressure generating means includes a piston located in a barrel part of the body of the pump, the piston being reciprocably movable in the barrel by means of a lever, conveniently releasably attached thereto. However, instead of a piston arrangement, a diaphragm could be used. Similarly, instead of a separate piston being provided, the two body parts of the pump could be constructed and arranged to be axially movable relative to each other to generate the required alternating pressure to cause lactation.

Lactation can result if a vacuum is created in the region of the nipple but the flow rate can be improved if the breast itself is stimulated in some way. Lactation is best promoted if an alternating pressure is created in the nipple region in a cyclic fashion, in other words a negative pressure is first created and then reduced or released, preferably by venting it to atmosphere. This can either be achieved on each stroke of the negative pressure generating means or several strokes can create a negative pressure to start lactation which is then released to provide the alternating pressure. In the preferred embodiment of the invention, the alternating pressure is created on each stroke of a piston but it will be appreciated that this is not essential to the invention.

Breast pumps are known in which a container to collect expressed milk is attached to the pump itself. In these pumps, the whole system including the empty container has to be de-pressurized before lactation will occur and also the user has to stimulate the breast to encourage lactation. The de-pressurisation of the whole system takes time and the negative pressure generated can sometimes be painful for the user or even dangerous. It is a feature of the present invention therefore that the valve system is mounted in the pump body in relation to the nipple receptacle and the negative pressure generation means so that only the region adjacent the nipple is subjected to the alternating pressure - not the milk collecting container when connected thereto.

Whilst the present invention is preferably concerned with a pump to which a baby feeding bottle can be releasably attached, e.g. by screw means, it will be appreciated that the container could with certain design modifications be integral or part of the pump.

BRIEF DESCRIPTION OF THE DRAWINGS

Several embodiments of the invention will now be described, by way of example only, with reference to the accompanying drawings, in which:

FIG. 5 shows the piston used in the pumps of FIGS. 1 to 3;
and
FIG. 6 shows the plug valve used in the pump of FIG. 1.

DETAILED DESCRIPTION

Figure 1A:
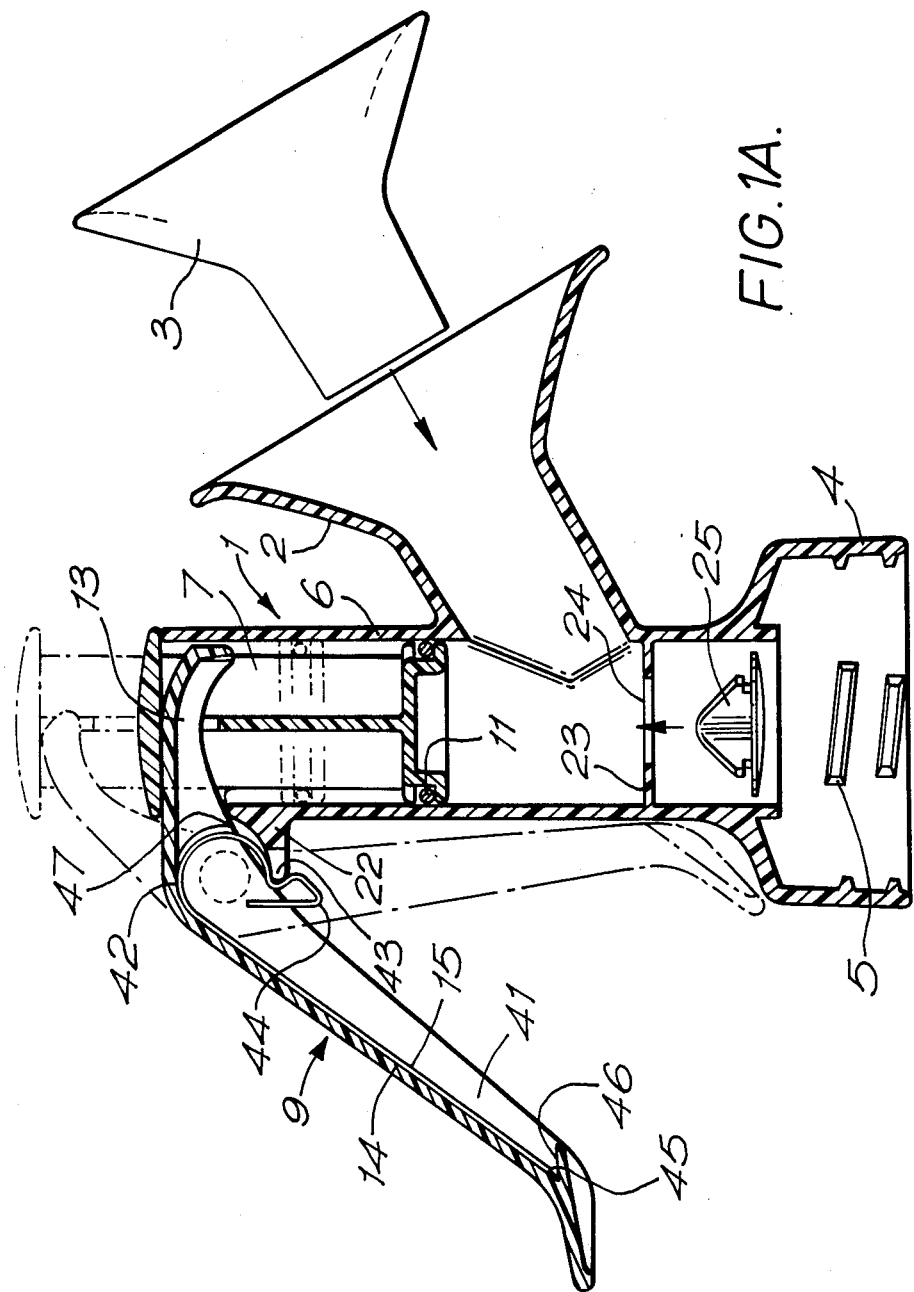
FIG. 1A shows the preferred form of pump.
Figure 1B:
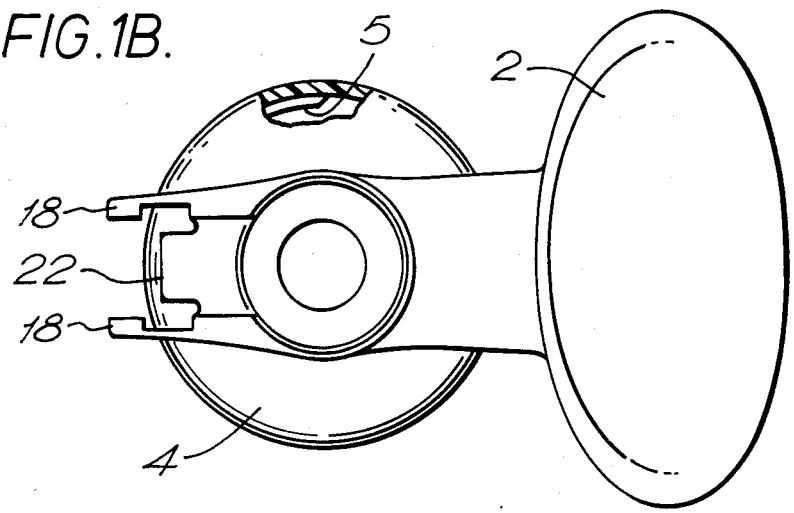
FIG. 1B is a plan view of the pump body of FIG. 1.
Figure 4:
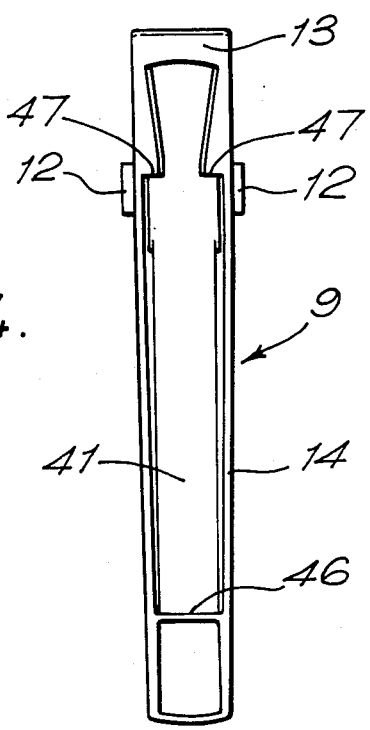
FIG. 4 is a plan view of the operating lever of the pump shown in FIGS. 1A and 1B.

Referring now the drawings, there is shown in FIGS. 1A and 1B a single handed breast pump comprising a body 1 having a first funnel shaped part 2 to receive and accommodate the nipple area of a users breast. In some instances, if the user has smaller breasts than normal, it may be necessary to fit a secondary breast shield 3 in the funnel part 2. The body 1 also includes a second part 4 which is provided with a screw thread 5 so that the pump can be attached to a container (not shown), preferably a feeding bottle in accordance with our UK Patent Application No. 8402664, for the collection of expressed milk. It is important that the screw threads do not make a seal with the milk collection container as the latter should desirably be maintained at atmospheric pressure.

The body 1 further includes a barrel portion 6 in which a piston 7 is slidably mounted. The piston 7 has an aperture 8 (see FIG. 5) in its upper part to receive end 13 of an actuating lever or trigger 9. The bottom part of the piston 7 is provided with an annular recess 10 to receive an O-ring 11, preferably made of silicone rubber, whose overall diameter is slightly larger than that of the barrel portion 6. The recess 10 is slightly deeper axially than the thickness of the O-ring to permit axial movement of the ring for reasons which will be explained hereafter. The upper surface of the recess 10 is provided with a pair or vent slots 20.

The barrel 6 is closed at its base adjacent the inlet from the funnel 2 by a wall 23 with a central hole 24 in it which receives a plug valve 25, preferably made of silicone rubber. As can be seen from FIG. 6, the valve comprises a disc part 26a of a larger diameter than the hole 24 and a plug part 26b made up from three webs 27 angularly spaced at 120°. Each web has an undercut 28 so that the plug valve can be push-fitted into the hole 24 and then be capable of axial movement therein.

The trigger 9 is of bell crank shape and comprises an operating lever portion 14 and a nose portion 13, the lever being cranked at the junction between the lever portion and the nose portion and having a pivot pin 12 on its opposite sides, each of which is shaped to fit in a slot 18 provided on the pump body (see Figure 1 B). The interior of the trigger is hollowed out into a cavity 41 to receive an actuating spring 15, preferably made of stainless steel. The spring 15 has a rounded end portion 42 which includes a detent 43 and a return portion 44.

In order to fit the spring 15 into the cavity 41 on the trigger, free end 45 is seated against ledge 46 and the remainder of the spring is pressed into the cavity 41. Due to the resilience of the spring 15, the diameter of its rounded end portion 42 is reduced as it is pressed against lip 47. Once it is past the lip, it springs back to its original diameter and seats against the reverse side of the lip and is thereby retained in the trigger. To remove the spring 15, for cleaning for instance, the return portion 44 is simply moved to the left as viewed in FIG. 1A until the diameter of the rounded end portion 42 is reduced sufficiently to clear the lip 47 so that the spring can be removed from the cavity 41.

As can be seen from FIGS. 1A and 1B, the pump is of extremely simple construction and readily dismantable so that it can be sterilised. To assemble the pump, the nose 13 of the trigger 9 with its spring 15 in position is loosely inserted into and through the hole 8 in the piston 7, the O-ring 11 having already been fitted into its recess 10.

This sub-assembly is then lowered so that the piston 7 slides into the barrel 6 and the pivot pins 12 on the trigger enter the slots 18 in the body 1. The assembly is then pushed down further until nose portion 22 on the pump body engages in the detent 43 in the spring 15. Once in this position, the trigger 9 cannot drop out of the body 6. To remove the trigger from the body however, the user simply presses the portion 44 of the spring 15 to the left as seen in FIG. 1 A to release the detent 43 from engagement with the nose 22 on the body. The assembly can then be lifted out of the slots 18.

The plug valve 25 is now fitted into the hole 24 with the webs 27 uppermost and the receptacle for collecting the expressed milk, preferably a feeding bottle, is screwed onto the bottom of the pump. The pump is now ready for use.

The operation of the pump is as follows. First of all, the user presses the funnel 2 against her breast with the nipple located centrally in the funnel. The trigger 9 can now be depressed into the position shown in outline in FIG. 1A. This movement raises the piston 7 with the O-ring making a seal with the wall of the barrel 6 and the bottom of its annular recess 10. At the commencement of the upward stroke, a negative pressure is created in the region between the nipple, the bottom of the piston 7 and the plug valve 25, which lifts the plug valve 25 into engagement with its seat around hole 24. As the upward stroke continues, a negative pressure is created in the region of the nipple until the top of the stroke is reached, momentarily holding the trigger in this raised position has the effect of assisting initial lactation. On release of pressure on the trigger, the piston is returned down the barrel 6 by the action of the spring 15 during which movement, the O-ring in the piston moves upwardly in its annular recess 10, thereby allowing the negative pressure in the pump to be relieved as it can vent to atmosphere past the inside diameter of the O-ring via the vent slots 20.

This creating of a negative pressure and releasing it in a cyclic basis stimulates the breast and lactation results, the expressed milk flowing past the valve into the container each time the valve is open.

Depending on the requirements of the user, either full or partial strokes can be used so it will be seen that the negative pressure applied to the nipple can readily be varied to suit the user.

Figure 2:
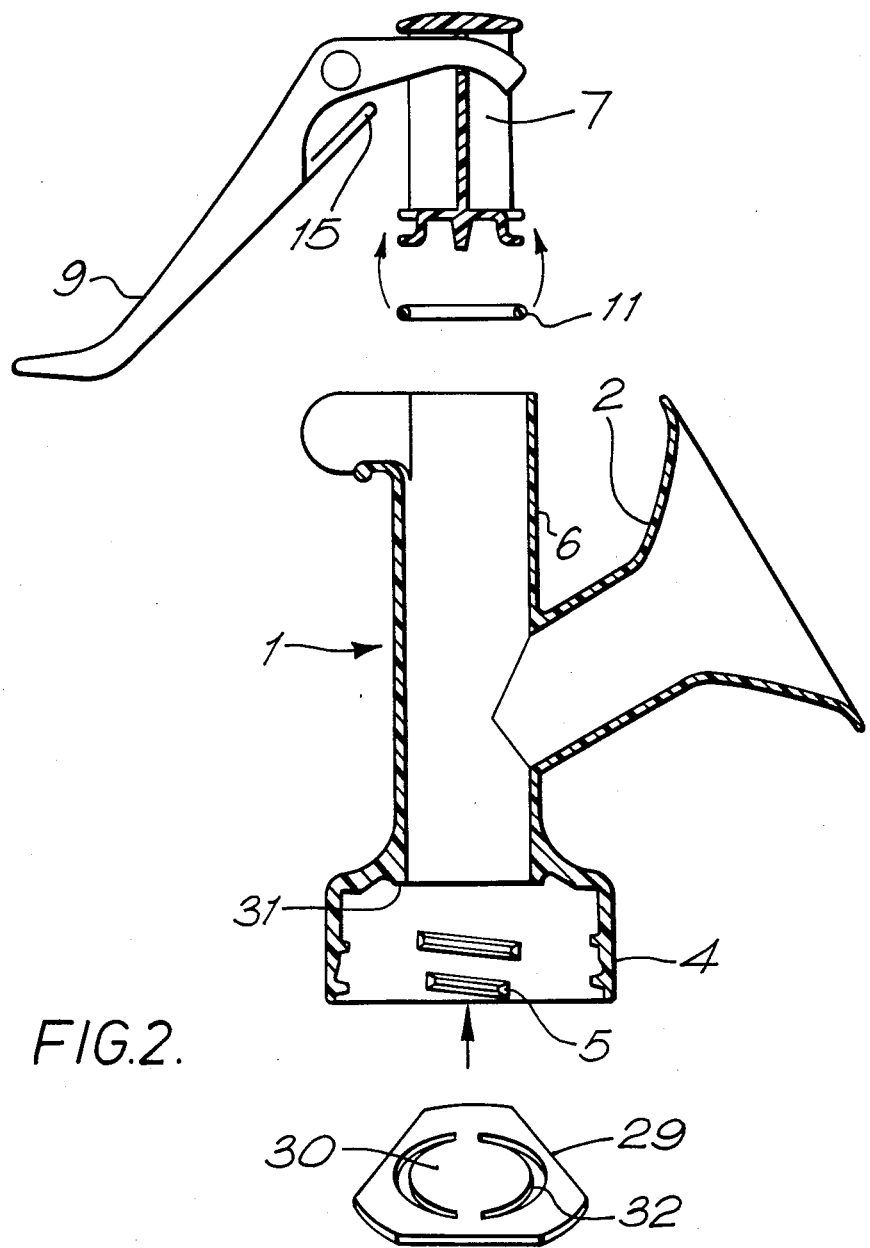
FIG. 2 shows an alternative pump.

Referring now to FIG. 2, a slightly different arrangement is shown in which a disc valve 29 is provided instead of the plug valve 25 and the lever 9 is biassed by means of spring finger 15. The disc valve is fitted immediately adjacent the screw threads 5 thereby providing a slightly larger volume to be de-pressurised whilst still maintaining atmospheric pressure in the collection container. The operation of the pump is much the same as that of FIG. 1 except that on the upward stroke, the central part 30 of the valve is lifted up into engagement with end collar 31 of the barrel 6 to make the required seal. On the downward stroke of the piston, it drops back to its rest position and the expressed milk flows through slots 32 into the collection container (not shown).

Figure 3:
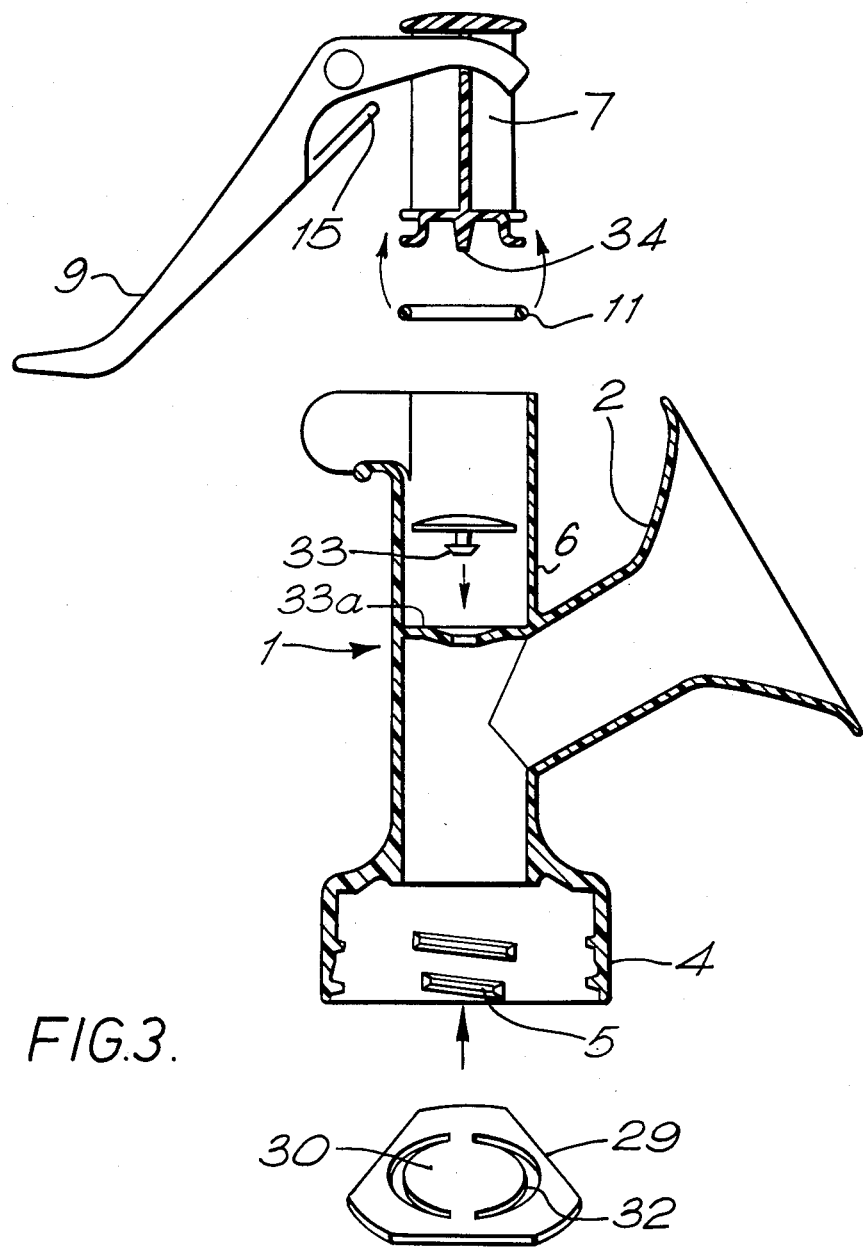
FIG. 3 shows another alternative pump.

FIG. 3 shows a still further embodiment similar to that of FIG. 2 but includes a wall 33a at the bottom of the barrel 6 having a hole in it to receive a second valve 33 in the form of a plug valve. The operation of this pump is again similar to that shown in FIG. 2 except that, on the upward stroke, the plug valve 33 is drawn away from its seat whereas the disc valve 29 is lifted against its seat so a negative pressure is created in the region between the users nipple in the funnel 2, the disc valve 29 and the bottom of the piston. However, on the downward stroke of the piston, the plug valve 33 is drawn against its seat by the negative pressure and the disc valve 29 is also kept in position against its seat so the negative pressure is retained. Further strokes of the piston result in the negative pressure being retained and increased and lactation will by now be taking place. However, the milk cannot reach the container screwed to the bottom of the pump until the negative pressure is released. This is done by lowering the piston until a projection 34 engages with the plug valve 33 and deforms it away from its seat. Once this happens, the disc valve 29 is allowed to drop away from its seat and the expressed milk can flow through the slots 32 as before into the container. This system is useful if the user needs a greater negative pressure to stimulate lactation that can be provided by a single stroke.

I claim:

1. A single-handed breast pump that may be held against the nipple of a breast by the user with one hand only, said pump comprising a tubular body having a barrel portion, a nipple receiving portion and a base portion for direct connection to a container to collect expressed milk, a piston reciprocable in the barrel portion by manually operable means, and including means to generate an alternating pressure at the nipple sufficient to express milk therefrom, a one-way valve in the base portion of the tubular body operable to prevent pressurization of a container when connected to the base portion, the nipple receiving portion being located on the body in a position such that a user can operate the piston with the same hand that is being used to hold the pump against the nipple, insert said means to generate an alternating pressure comprising an annular seal means axially displaceable in an annular groove in the piston, the piston also having at least one vent hole communicating with the annular groove.

2. A single-handed breast pump adapted so that it may be held against the nipple of a breast by the user with one hand only, said pump comprising a tubular body having a barrel portion, a nipple receiving portion and a base portion for direct connection to a container to collect expressed milk, a piston reciprocable in the barrel portion by manually operable means and including means to generate an alternating pressure at the nipple sufficient to express milk therefrom, a first one-way valve in the base portion of the tubular body operable to prevent pressurization of a container when connected to the base portion, the nipple receiving portion being located on the body in a position such that a user can operate the piston with the same hand that is being used to hold the pump against the nipple, wherein a second one-way valve is provided between the piston and the one-way valve in the base part, said valves being operable on activation of the manually operable means to pressurize the volume between said valves and the nipple, the piston having a part protruding from its end which can be brought into engagement with said second valve to deform it and release the pressure in said volume and allow milk to flow into a container when connected to the base part.

3. A manually operable single-handed breast pump for collecting expressed milk in a receptacle, comprising: a pump body having a body axis and including a breast-receiving portion extending laterally of the body axis, a base portion and a barrel portion coaxial with said base portion said base portion and said barrel portion having axes coincident with said body axis, said breast receiving portion disposed intermediate the base and barrel portions, means in said base portion for connection to said receptacle to collect expressed milk, a one-way valve mounted in said base portion, a piston acting along an axis coincident with said body axis, a lever operatively secured with said piston, said barrel portion housing said piston, said piston being reciprocally moveable therein by means of said lever which is connected thereto, said lever being mounted on the pump body for movement in the direction generally normal to the axis of said pump body, said piston having means operable on reciprocal movement of the lever and piston to generate an alternating pressure in the pump body and breast receiving portion only, the pump being constructed and arranged so that it may be held against the user's breast with one hand only, the same hand being used to cyclically move the lever to generate said alternating pressure to cause milk to be expressed from the breast.

4. A pump as claimed in claim 3 wherein the one-way valve is a plug valve mounted in a hole in a wall extending across the pump body in said base portion.

5. A pump as claimed in claim 3 wherein the lever is detachably connected to the piston and is operable against the action of a resilient bias, the lever being pivotally mounted on the pump body so as to be located within hand width of the breast receiving portion so that the same hand can be used to activate said lever as is used to hold the pump against the breast.

6. A pump as claimed in claim 3 wherein the barrel portion, breast receiving portion and base portion of the pump body are integrally formed.

7. A pump as claimed in claim 3 wherein the piston valve means comprises an annular seal means displaceable in an annular groove in the piston, the piston also having at least one vent slot communicating with said annular groove.

8. A pump as claimed in claim 3 wherein a second one-way valve is provided between the piston and the one-way valve on the base part, said valves being operable on activation of the lever to pressurize the volume between said valves and the nipple, the piston having a part protruding from its end which can be brought into engagement with said second valve to distort it and release the pressure in said volume and allow milk to flow into a container when connected to the base part.

9. A pump as claimed in claim 3 wherein the means to generate an alternating pressure which includes an annular seal means having piston open and closed positions and being responsive to the movement of said piston in opposite directions under control of said lever to cycle between these open and closed positions.

10. A pump as claimed in claim 9 wherein the annular seal means is controlled by piston movement in a first direction for closing thereof to enable pressurization of the breast receiving portion.

11. A pump as claimed in claim 10 wherein the one-way valve also has open and closed positions, and is moved to its closed position in direct response to piston movement in said first direction.

12. A pump as claimed in claim 11 wherein the one-way valve is moved to its open position in response to piston movement in said second direction.

13. A pump as claimed in claim 10 wherein the annular seal means is controlled by piston movement in a second direction, opposite to said first direction, for opening thereof, to relieve negative pressure at the breast receiving portion.

14. A pump as claimed in claim 13 wherein the annular seal means has vent means enabling venting to atmosphere.

15. A pump as claimed in claim 3 wherein the lever is disposed at a position substantially diametrically opposite to said breast receiving portion.

16. A pump as claimed in claim 15 wherein the lever has a normally biased position extending from said body and a depressed position in which the lever extends substantially in parallel to said body axis.

* * * * *